(12) United States Patent
Lavik

(10) Patent No.: US 9,962,462 B2
(45) Date of Patent: May 8, 2018

(54) DRY SPRAY ON HEMOSTATIC SYSTEM

(71) Applicant: CASE WESTERN RESERVE UNIVERSITY, Cleveland, OH (US)

(72) Inventor: Erin Lavik, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days. days.

(21) Appl. No.: 15/180,889

(22) Filed: Jun. 13, 2016

(65) Prior Publication Data

US 2017/0043051 A1    Feb. 16, 2017

Related U.S. Application Data

(60) Provisional application No. 62/174,358, filed on Jun. 11, 2015.

(51) Int. Cl.
*A61L 26/00* (2006.01)
*C08G 81/00* (2006.01)

(52) U.S. Cl.
CPC ....... *A61L 26/0066* (2013.01); *A61L 26/0019* (2013.01); *A61L 26/0047* (2013.01); *A61L 26/0076* (2013.01); *C08G 81/00* (2013.01); *A61L 2300/222* (2013.01); *A61L 2300/252* (2013.01); *A61L 2300/418* (2013.01); *A61L 2300/624* (2013.01); *A61L 2400/04* (2013.01); *A61L 2400/12* (2013.01); *C08G 2650/02* (2013.01); *C08G 2650/38* (2013.01)

(58) Field of Classification Search
None
See application file for complete search history.

(56) References Cited

U.S. PATENT DOCUMENTS

| | | | |
|---|---|---|---|
| 2004/0180438 A1* | 9/2004 | Pachuk | C12N 15/111 435/455 |
| 2006/0002861 A1* | 1/2006 | Biggadike | A61K 9/0075 424/46 |
| 2006/0140923 A1 | 6/2006 | Evangelista et al. | |
| 2007/0066552 A1* | 3/2007 | Clarke | A61K 8/606 514/44 R |
| 2009/0130692 A1* | 5/2009 | Kolmar | A61K 38/56 435/7.21 |
| 2011/0052712 A1* | 3/2011 | Eaton | A61K 9/0014 424/493 |
| 2011/0250284 A1 | 10/2011 | Lavik et al. | |
| 2013/0243832 A1 | 9/2013 | Turos et al. | |

FOREIGN PATENT DOCUMENTS

| | | |
|---|---|---|
| WO | WO-2010/008792 A1 | 1/2010 |
| WO | WO-2011/106702 A2 | 9/2011 |
| WO | WO-2012/061703 A1 | 5/2012 |
| WO | WO-2012/068476 A2 | 5/2012 |
| WO | WO-2012-142362 A2 | 10/2012 |
| WO | WO-2013/106117 A2 | 7/2013 |

OTHER PUBLICATIONS

Lavik et al. (WO 2013106117 A2).*
Aggleton et al., Lesions of the rat perirhinal cortex spare the acquisition of a complex configural visual discrimination yet impair object recognition. *Behav. Neurosci.* 124(1): 55-68 (2010).
Baker et al., Effects of exogenous ubiquitin in a polytrauma model with blunt chest trauma. *Crit. Care Med.* 40: 2376-84 (2012).
Bertram et al., Intravenous hemostat: nanotechnology to halt bleeding. *Sci. Translational Med.* 1: 11 ra22 (2009).
Blajchman, Substitutes and alternatives to platelet transfusions in thrombocytopenic patients. *J. Thromb. Haemost.* 1: 1637-41(2003).
Blajchman, Substitutes for success. *Nat. Med.* 5: 17-8 (1999).
Frink et al., Experimental trauma models: an update. *J. Biomed. Biotech.* 2011: 979383 (2011).
Gegel et al., The effects of BleedArrest on hemorrhage control in a porcine model. *US Army Med. Depart. J.* 31-35 (2012).
Gurney et al., A hemoglobin based oxygen carrier, bovine polymerized hemoglobin (HBOC-201) versus Hetastarch (HEX) in an uncontrolled liver injury hemorrhagic shock swine model with delayed evacuation. *J. Trauma* 57: 726-38 (2004).
Johnson et al., Histamine release associated with intravenous delivery of a fluorocarbon-based sevoflurane emulsion in canines. *J. Pharma. Sci.* 100: 2685-92 (2011).
Johnson et al., The effects of QuikClot Combat Gauze on hemorrhage control in the presence of hemodilution. *US Army Med. Depart. J.* 36-39 (2012).
Kim et al., Toward 21st century blood component replacement therapeutics: artificial oxygen carriers, platelet substitutes, recombinant clotting factors, and others. *Artif. Cells Blood Substit. Immobil. Biotechnol.* 34: 537-50 (2006).
Kim et al., Chronic NMDA administration to rats increases brain pro-apoptotic factors while decreasing anti-Apoptotic factors and causes cell death. BMC Neurosci, 10: 123 (2009).
Lee et al., Novel treatment modalities: new platelet preparations and substitutes. *Br. J. Haematol.* 114: 496-505 (2001).
Sallinen et al., Pharmacological characterization and CNS effects of a novel highly selective alpha2C-adrenoceptor antagonist JP-1302. *Br. J. Pharmacol.* 150(4): 391-402 (2007).
Siller-Matula et al., Interspecies differences in coagulation profile. *Thromb. Haemost.* 100: 397-404 (2008).
Szebeni et al., Liposome-induced complement activation and related cardiopulmonary distress in pigs: factors promoting reactogenicity of Doxil and AmBisome. *Nanomedicine*, 8: 176-84 (2012).
VandeVord et al., Mild neurotrauma indicates a range-specific pressure response to low level shock wave exposure. *Ann. Biomed. Eng.* 40(1): 227-36 (2012).

* cited by examiner

*Primary Examiner* — Robert A Wax
*Assistant Examiner* — Quanglong N Truong
(74) *Attorney, Agent, or Firm* — Marshall, Gerstein & Borun LLP

(57) ABSTRACT

The invention provides for dry spray compositions comprising co-polymers comprising a core, water-soluble polymer and a peptide.

9 Claims, 3 Drawing Sheets

DRY SPRAY ON HEMOSTATIC SYSTEM

This application claims priority to U.S. Provisional Patent Application No. 62/174,358, filed Jun. 11, 2015, which is incorporated herein by reference in its entirety.

This invention was made with government support under grant number OD007338 awarded by the National Institutes of Health (NIH). The government has certain rights in the invention.

FIELD OF INVENTION

The invention provides for dry spray compositions comprising a co-block polymer coupled a water soluble polymer.

BACKGROUND

Hemorrhaging is also the first step in the injury cascade, for example, in the central nervous system (CNS). In both spinal cord and traumatic brain injuries, the first observable phenomena, regardless of mechanism of insult, is hemorrhaging. If one can stop the bleeding, presumably one can preserve tissue and improve outcomes. The primary mechanical insult is very often a small part of the injury. The secondary injury processes that occur over hours, days, and weeks following injury lead to progression and the poor functional outcomes. Stopping those secondary injury processes would mean preservation of greater amounts of tissue. Preservation of tissue means better functional outcomes.

Following injury, hemostasis is established through a series of coagulatory events. The critical steps in terms of platelets involve their activation, binding, and release of a host of growth factors and other molecules including fibrinogen. During vascular injury, collagen is exposed which triggers the activation of platelets. Platelet morphology shifts from a discoid to stellate, and they adhere to the exposed collagen. Once platelet aggregation begins, several inflammatory agents are released from their storage granules including adenosine diphosphate (ADP), which causes the surfaces of nearby circulating platelets to become adherent. Serotonin, epinephrine, and thromboxane A 2 further induce extreme vasoconstriction. The ultimate step, clot formation, is the conversion of fibrinogen, a large, soluble plasma protein produced by the liver and normally present in the plasma, into fibrin, an insoluble, threadlike molecule.

In severe injuries, these endogenous processes fall short and uncontrolled bleeding results. There have been a number approaches to augment these processes and induce hemostasis beyond the external methods. Platelet substitutes which either replace or augment the existing platelets have been pursued for a number of years (Blajchman, *J. Thromb. Haemost.* 1: 1637-41 (2003)). Administration of allogeneic platelets can help to halt bleeding; however, platelets have a short shelf life, and administration of allogeneic platelets can cause graft versus host disease, alloimmunization, and transfusion-associated lung injuries (Blajchman, *J. Thromb. Haemost* 1: 1637-41 (2003)). Non-platelet alternatives including red blood cells modified with the Arg-Gly-Asp (RGD) sequence, fibrinogen-coated microcapsules based on albumin, and liposomal systems have been studied as coagulants (Siller-Matula et al., *Thromb. Haemost* 100: 397-404 (2008)), but toxicity, thrombosis, and limited efficacy are major issues in the clinical application of these products (Frink et al. *J. Biomed. Biotech.* 2011: 979383 (2011)).

There are a number of approaches to augment hemostasis in the field and clinic including pressure dressings, absorbent materials such as QuikClot®, and intravenous (W) infusion of activated recombinant factor VII (rFVIIa), but the former two are only applicable to exposed wounds, and rFVIIa has had both mixed results, requires refrigeration, and is expensive making it challenging to administer in the field or at the site of trauma. Clearly, a new approach to halt bleeding that is amenable to administration in the field is needed.

Spray on hemostatic systems have many advantages such as quick and even distribution over a broad coverage area. Spray on hemostatic systems can be easily applied to areas that are difficult to contact by swabs or bandages. There is a need for development of spray on systems hemostatic systems.

For a hemostat to be effective for complex trauma, the system needs to be non-toxic, stable when stored at room temperature (i.e. a medic's bag), have the potential for immediate. administration, and possess injury site-specific aggregation properties so as to avoid non-specific thrombosis. For this system to be clinically translatable, ideally it needs to be made with materials previously approved by the FDA. Practically, it also needs to be affordable.

SUMMARY OF INVENTION

The present invention provides for dry spray hemostatic systems that allow for quick and even distribution of hemostatic nanoparticles or synthetic platelets that reducing bleeding and improve outcomes in trauma. The invention provides for dry spray compositions comprising a co-block polymer coupled to a water soluble polymer.

The invention provides for dry spray compositions which comprise nanoparticles that halve bleeding time in a femoral artery injury model, which allow for even distribution of the nanoparticles at a wound site and allow application to areas that are difficult to contact with other methods of administration. These nanoparticles act essentially as synthetic platelets and are stable at room temperature.

In one aspect, any of the dry spray compositions of the invention comprise a co-block polymer, wherein the co-block polymer is a nanoparticles comprising a core, a water soluble polymer and a peptide. In a particular embodiment, the water soluble polymer of the spray composition is attached to the core at a first terminus of the water soluble polymer. In addition, the peptide of the spray composition comprises an RGD amino acid sequence.

In another aspect, any of the dry spray compositions of the invention further comprise a polycation. For example, the invention provides for dry spray compositions in which the polycation is positioned adjacent the co-block polymer and the water soluble polymer.

In any of the dry spray compositions of the invention, the co-block polymer is a diblock copolymer, a triblock copolymer, an amphiphilic block copolymer or a PEG block co-polymer. For examples, the co-block polymer is poly (lactide-co-glycolide acid (PLGA), polylactic acid (PLA), polyglycolide (PGA), polycaprolactone (PCL), poly(ϵ-caprolactone), poly-L-lysine (PLL) or combinations thereof.

This dry spray compositions of the invention are effective over a very wide polymer or nanoparticle concentration, e.g. at a concentration of 0.1% nanoparticles, 0.2% nanoparticles, 0.3% nanoparticles, 0.4% nanoparticles, 0.5% nanoparticles, 0.6% nanoparticles, 0.7% nanoparticles, 0.8% nanoparticles, 0.9% nanoparticles, 1.0% nanoparticles, 2.0% nanoparticles, 3.0% nanoparticles, 4.0% nanoparticles, 5.0% nanoparticles, 6.0% nanoparticles, 7.0% nanoparticles, 8.0% nanoparticles, 9.0% nanoparticles, 10% nanoparticles, 15% nanoparticles, 20% nanoparticles, 25% nanoparticles, 30% nanoparticles, 35% nanoparticles, 40% nanoparticles, 45% nanoparticles, 50% nanoparticles, 55% nanoparticles, 60% nanoparticles, 65% nanoparticles, 70% nanoparticles, 75% nanoparticles, 80% nanoparticles, 85% nanoparticles, 90% nanoparticles, 95% nanoparticles, or 99% nanoparticles.

This dry spray compositions of the invention may range from 0.1% to 99% nanoparticles, 0.1% to 0.25% nanoparticles, 0.1% to 0.5% nanoparticles, 0.1% to 0.75% nanoparticles, 0.1% to 10% nanoparticles, 0.5% to 0.75% nanoparticles, 0.5% to 1% nanoparticles, 0.5% to 25% nanoparticles, 1% to 10% nanoparticles, 1% to 20% nanoparticles, 1% to 30% nanoparticles, 5% to 10% nanoparticles, 5% to 25% nanoparticle, 5% to 50% nanoparticles, 10% to 20% nanoparticles, 10% to 30% nanoparticles, 10% to 50% nanoparticles, 10% to 75% nanoparticles, 20% to 30% nanoparticles, 20% to 40% nanoparticles, 20% to 50% nanoparticles, 20% to 60% nanoparticles, 20% to 30% nanoparticles, 20% to 40% nanoparticles, 20% to 50% nanoparticles, 20% to 75% nanoparticles, 20% to 80% nanoparticles, 30% to 40% nanoparticles, 30% to 40% nanoparticles, 30% to 50% nanoparticles, 30% to 60% nanoparticles, 30% to 70% nanoparticles, 30% to 80% nanoparticles, 30% to 90% nanoparticles, 40% to 50% nanoparticles, 40% to 60% nanoparticles, 40% to 70% nanoparticles, 40% to 80% nanoparticles, 40% to 90% nanoparticles, 50% to 60% nanoparticles, 50% to 75% nanoparticles, 50% to 80% nanoparticles, 50% to 90% nanoparticles, 50% to 95% nanoparticles, 60% to 70% nanoparticles, 60% to 75% nanoparticles, 60% to 80% nanoparticles, 60% to 85% nanoparticles, 60% to 90% nanoparticles, 60% to 95% nanoparticles, 70% to 75% nanoparticles, 70% to 80% nanoparticles, 70% to 85% nanoparticles, 70% to 90% nanoparticles, 70% to 95% nanoparticles, 75% to 90% nanoparticles, 75% to 95% nanoparticles, 75% to 98% nanoparticles, 80% to 90% nanoparticles, 80% to 85% nanoparticles, 80% to 90% nanoparticles, 80% to 95% nanoparticles, 80% to 98% nanoparticles, 80% to 99% nanoparticles or 90% to 98% nanoparticles.

In any of the dry spray compositions of the invention, the water soluble polymer is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly (1-hydroxymethylethylene hydroxymethylformal) (PHF), 2-methacryloyloxy-2'-ethyltrimethylammoniumphosphate (MPC), polyethylene glycol propionaldehyde, copolymers of ethylene glycol/propylene glycol, monomethoxy-polyethylene glycol, carboxymethylcellulose, polyacetals, poly-1, 3-dioxolane, poly-1,3,6-trioxane, ethylene/maleic anhydride copolymer, poly (β-amino acids) (either homopolymers or random copolymers), poly(n-vinyl pynolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and combinations or mixtures thereof.

For example, the invention provides for dry spray compositions comprising nanoparticles comprising the water soluble polymer PEG, such as PEG having an average molecular weight between 100 Da and 10,000 Da.

The invention provides for dry spray compositions wherein the polycation is selected from polylysine, polyarginine, polyornithine, polyhistidine, cationic polysaccharides, POLYBRENE® (1,5-dimethyl-1,5-diazaundecamethylene polymethobromide, hexadimethrine bromide), histone, myelin basic protein, polymyxin B sulfate, dodecyltrimethylammonium bromide, bradykinin, spermine, putrescine, cadaverine, octylarginine, cationic dendrimer, and synthetic peptides. In particular, the invention provides for spray compositions wherein the polycation is polylysine.

In any of the dry spray compositions of the invention, the nanoparticles comprise a peptide comprising a sequence selected from the group consisting of RGD, RGDS (SEQ ID NO: 1), GRGDS (SEQ ID NO: 2), GRGDSP (SEQ ID NO: 3), GRGDSPK (SEQ ID NO: 4), GRGDN (SEQ ID NO: 5), GRGDNP (SEQ ID NO: 6), GGGGRGDS (SEQ ID NO: 7), GRGDK (SEQ ID NO: 8), GRGDTP (SEQ ID NO: 9), cRGD, YRGDS (SEQ ID NO: 10) or variants thereof. The dry spray compositions of the invention may comprise a nanoparticle comprising a RGD peptide that is in a tandem repeat. The dry spray compositions of the invention may comprise nanoparticles comprising 2, 3, 4, 5, 6, 7, 8, 9, 10 or more copies of the RGD peptide or the nanoparticles comprising multiple copies of the RGD peptide. For example, the dry spray composition comprises nanoparticles comprising multiple copies of the RGD peptide and wherein all copies of the RGD peptide are the same or the dry spray composition comprises nanoparticles comprising multiple copies of the RGD peptide and wherein two copies of the RGD peptide have different sequences.

For example, the invention also provides for dry spray composition comprising a nanoparticle, the nanoparticle comprising a core, a water soluble polymer and a peptide, the water soluble polymer attached to the core at a first terminus of the water soluble polymer, the peptide attached to a second terminus of the water soluble polymer, the peptide comprising an RGD amino acid sequence, the water soluble polymer of having sufficient length to allow binding of the peptide to glycoprotein IIb/IIIa (GPIIb/IIIa), the composition optionally further comprising a poloxamer. The nanoparticles in the compositions of the invention are neutrally charged such as nanoparticles having a zeta potential of about −3.0 mV to about 3 mV.

The dry spray compositions of the invention include those in which the poloxamer is present at about 0.1% to about 60% of the composition. The invention also provides for compositions wherein the poloxamer is present at about 0.1% to about 40% of the composition.

In addition, dry spray compositions of the invention include those in which the poloxamer in the composition is present up to 50 times nanoparticle mass.

In any of the dry spray compositions of the invention, the poloxamer is a non ionic triblock copolymer comprising a structure -[hydrophilic polymer-hydrophobic polymer-hydrophilic polymer]n-.

In any of the dry spray composition of the invention, the poloxamer is -[polyethylene glycol-poly(propylene oxide)-polyethylene glycol]n-. For example, the poloxamer may be selected from the group consisting of poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407 and Kolliphor P 188. In addition, the poloxamer may be selected from the group consisting of Pluronic® 10R5, Pluronic® 17R2, Pluronic® 17R, Pluronic® 25R2, Pluronic® 25R4, Pluronic® 31R1, Pluronic® F 108 Cast Solid Surfacta, Pluronic® F 108 NF, Pluronic® F 108 Pastille, Pluronic® F 108NF Prill Poloxamer 338, Pluronic® F 127, Pluronic® F 127 NF, Pluronic® F 127 NF 500 BHT Prill, Pluronic® F 127 NF Prill Poloxamer 407, Pluronic® F 38, Pluronic® F 38 Pastille, Pluronic® F 68, Pluronic® F 68 Pastille, Pluronic® F 68 LF Pastille, Pluronic® F 68 NF, Pluronic® F 68 NF Prill Poloxamer 188, Pluronic® F 77, Pluronic® F 77 Micropastille, Pluronic® F 87, Pluronic® F 87 NF, Pluronic® F 87 NF Prill Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 44 NF, Poloxamer 124, Pluronic® L 61, Pluronic® L 62, Pluronic® L 62 LF, Pluronic® L 62D, Pluronic® L 64, Pluronic® L 81, Pluronic® L 92, Pluronic® L44 NF, Pluronic® N 3, Pluronic® P 103, Pluronic® P 104, Pluronic® P 105, Pluronic® P 123 Surfactant, Pluronic® P 65, Pluronic® P 84, and Pluronic® P 85.

In particular, the invention provides for a dry spray composition comprising a nanoparticle, the nanoparticle comprising a core, a water soluble polymer and a peptide, the water soluble polymer attached to the core at a first terminus of the water soluble polymer, the peptide attached to a second terminus of the water soluble polymer, the peptide comprising an RGD amino acid sequence, the water soluble polymer having sufficient length to allow binding of the peptide to glycoprotein IIb/IIIa (GPIIb/IIIa), the composition further comprising a poly(acrylic acid), and a polycation such as polylysine. The nanoparticles of the dry spray composition may have a neutral charge or have a zeta potential of about −3.0 mV to about 3.0 mV.

In any of the dry spray compositions of the invention, the composition comprises nanoparticles having a spheroid shape and a diameter of less than 1 micron. For example, the nanoparticles has a diameter between 0.1 micron and 1 micron.

Alternatively, in any of the dry spray compositions of the invention, the composition comprises nanoparticles having a non-spheroid shape. For example, the nanoparticle is a rod, fiber or whisker. The nanoparticles may have an aspect ratio length to width of at least 3.

The invention provides for any of the foregoing dry spray compositions that are stable at room temperature for at least 14 days.

The invention also provides for any of the foregoing dry spray composition comprising nanoparticles having a core that is a crystalline polymer. In addition, any of the foregoing spray compositions comprise nanoparticles having a core that is a single polymer, a block copolymer, a triblock copolymer or a quadblock polymer. For example, the dry spray compositions of the invention comprise nanoparticles having a core comprising PLGA, PLA, PGA, (poly (ϵ-caprolactone) PCL, PLL or combinations thereof.

The invention provides for dry spray compositions comprising nanoparticles having a biodegradable core or alternatively a non-biodegradable core. In any of the compositions of the invention, the nanoparticles may have a solid core. For example, the invention provides for spray compositions comprising nanoparticles wherein the core is a material of gold, silver, platinum, aluminum, palladium, copper, cobalt, indium, nickel, ZnS, ZnO, Ti, $TiO_2$, Sn, $SnO_2$, Si, $SiO_2$, Fe, $Fe^{+4}$, steel, cobalt-chrome alloys, Cd, CdSe, CdS, and CdS, titanium alloy, AgI, AgBr, $HgI_2$, PbS, PbSe, ZnTe, CdTe, $In_2S_3$, $In_2Se_3$, $Cd_3P_2$, $Cd_3As_2$, InAs, GaAs, cellulose or a dendrimer structure.

In any of the dry spray compositions of the invention, the composition comprises nanoparticles comprising a water soluble polymer attached to the core at a molar ratio of 0.1:1 to 1:10 or greater.

In any of the dry spray composition of the invention, the composition comprises nanoparticles further comprising a therapeutic compound. For example, the therapeutic compound is hydrophobic. Alternatively, the therapeutic compound is hydrophilic. The therapeutic compound may be covalently attached to the nanoparticle, non-covalently associated with the nanoparticle, associated with the nanoparticle through electrostatic interaction, or associated with the nanoparticle through hydrophobic interaction. The therapeutic compound may be a growth factor, a cytokine, a steroid, or a small molecule or an anti-cancer compound.

The invention provides for dry spray compositions which are pharmaceutical compositions, wherein the composition further comprises a pharmaceutically acceptable carrier or formulation.

The invention provides for methods of treating a condition in an individual comprising the step of administering any of the foregoing dry spray compositions to a patient in need thereof in an amount effective to treat the condition. For example, the invention provides for methods wherein the individual has a bleeding disorder and the dry spray composition is administered in an amount effective to reduce bleeding. In particular, the invention provide for methods of treating a bleeding disorder comprising the step of administering any of the foregoing spray compositions in an amount effective to reduce bleeding time by more than 15% compared to no administration or administration of saline. In these methods of the invention, the bleeding disorder may be a symptom of a clotting disorder, thrombocytopenia, wound healing disorder, trauma, blast trauma, a spinal cord injury or hemorrhaging.

The invention also provides for use of any of the dry spray compositions of the invention for the preparation of a medicament for the treatment of a condition wherein the medicament comprises the spray composition in an amount effective to treat the condition. For example, the invention provides for an use of any of the foregoing dry spray compositions of the invention for the preparation of a medicament for the treatment of a bleeding disorder wherein the medicament comprises the dry spray composition in an amount effective to reduce bleeding. The invention provides for an use of any of the foregoing compositions for the preparation of a medicament for the treatment of a bleeding disorder wherein the medicament comprise the dry spray composition in an amount effective to reduce bleeding time by more than 15% compared to no administration or administration of saline. In any of the uses of the invention, the medicament may be administered to treat a bleeding disorder that is a symptom of a clotting disorder, thrombocytopenia, a wound healing disorder, trauma, blast trauma, a spinal cord injury or hemorrhaging.

The invention also provides for dry spray compositions of the invention for treating a condition such as a bleeding disorder. The invention provides for dry spray compositions for treating a bleeding disorder wherein the bleeding disorder is a symptom of a clotting disorder, thrombocytopenia, a wound healing disorder, trauma, blast trauma, a spinal cord injury or hemorrhaging. The invention provides for dry spray compositions for the treatment of a bleeding disorder wherein the spray composition is administered in an mount effective to reduce bleeding time by more than 15% compared to no administration or administration of saline.

DETAILED DESCRIPTION

Compositions comprising a functionalized nanoparticle is provided based on FDA-approved materials that has multiple uses. In various aspects, the nanoparticle reduces bleeding time at the site of injury, plays a role in hemostasis following trauma to the central nervous system (CNS) and provides a means for localized drug delivery.

Intravenous administration of hemostatic nanoparticles that target activated platelets have been investigated by a number of groups with some promise and a range of challenges. RGD conjugated red blood cells (RBCs) called thromboerythrocytes showed promise in vitro but did not significantly reduce prolonged bleeding times in thrombocytopenic primates. Fibrinogen-coated albumin microparticles, "Synthocytes" and liposomes used by others carrying the fibrinogen γ chain dodecapeptide (HHLGGAKQAGDV (SEQ ID NO: 11)) showed success in bleeding models in thrombocytopenic rabbits. However, Synthocytes were ineffective in treating bleeding in normal rabbits, and the liposomes do not appear to have yet been studied for this purpose.

The dry spray compositions of the invention are an improvement over intravenous administration of the nanoparticles of the invention because the spray allows for quick and even distribution of the nanoparticles at the site of the wound, which enhances wound healing and more efficiently mitigates bleeding. In addition, the dry spray compositions may be applied over a broad coverage area in a short period of time and allows for a controls and continuous supply to the affected area. Dry spray compositions allow for the synthetic platelets to be easily applied in awkward or hard to reach areas.

The experiments provided herein demonstrate that the hemostatic nanoparticles of the invention reduced bleeding. The dry spray compositions evenly distribute the hemostatic nanoparticles of the invention which will allow of easy and quick application and enhance the ability to reduce bleeding.

The invention provides for dry spray compositions comprising a nanoparticle, and a polycation, the nanoparticle comprising a core, a water soluble polymer and a peptide, the water soluble polymer attached to the core at a first terminus of the water soluble polymer, the peptide attached to a second terminus of the water soluble polymer, the peptide comprising an RGD amino acid sequence, the water soluble polymer of having sufficient length to allow binding of the peptide to glycoprotein IIb/IIIa (GPIIb/IIIa). The compositions may further comprise a poloxamer.

Figure 1:
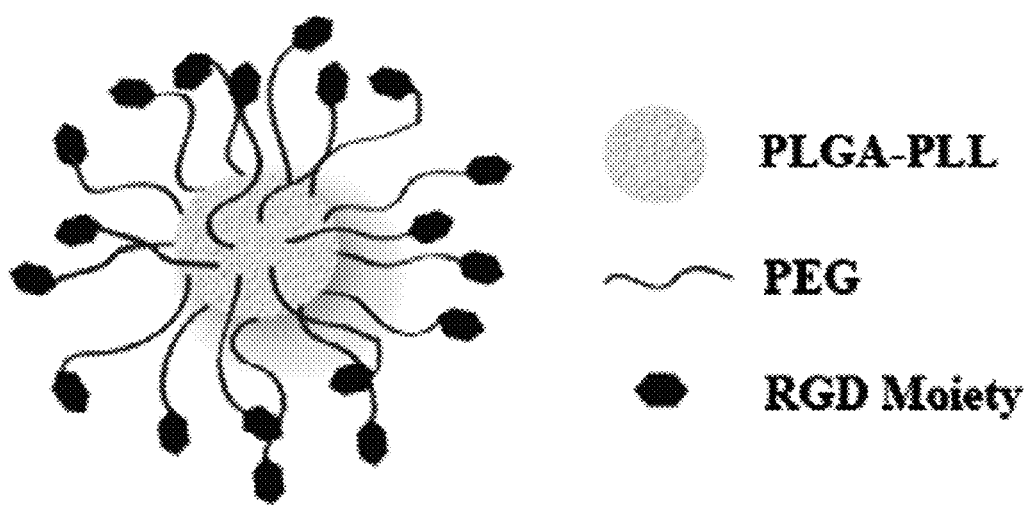
FIG. 1 provides a schematic of the PLGA-PLL nanoparticles of the invention.

An exemplary nanoparticle of the invention is set out in FIG. 1 which comprises a PLGA-PLL nanosphere core (~200 nm), PEG arms conjugated to the core at the first terminus and conjugated to RGD peptides conjugated to the PEG arms at the second terminus. This nanoparticle binds to activated platelets. The attributes of the nanoparticles of the invention include specificity for a vascular injury site, biocompatible and biodegradable. In addition, the nanoparticles may be stored dry at room temperature and have a rapid and easy administration.

Nanoparticles

The disclosure provides a nanoparticle comprising a core, a water soluble polymer and a peptide, the water soluble polymer attached to the core at a first terminus of the water soluble polymer, the peptide attached to a second terminus of the water soluble polymer, the peptide comprising an RGD amino acid sequence, the water soluble polymer of having sufficient length to allow binding of the peptide to glycoprotein IIb/IIIa (GPIIb/IIIa). In various aspects, the peptide is linear or cyclic. It will be appreciated that in a composition comprising a plurality of nanoparticles of the disclosure, the composition is contemplated to include nanoparticles wherein all peptides are linear, all peptides are cyclic, or a mixture of linear and cyclic peptides is present.

Nanoparticles of the disclosure are temperature stable in that they maintain essentially the same structure and/or essentially the same function over a wide range of temperatures. By "essentially the same structure" and "essentially the same function," the disclosure contemplates "essentially the same" to mean without a change that affects the ability of the nanoparticles to carry out its use at a dosage of plus or minus 10% of an original dosage, plus or minus 10% of an original dosage, plus or minus 10% of an original dosage, plus or minus 9% of an original dosage, plus or minus 8% of an original dosage, plus or minus 7% of an original dosage, plus or minus 6% of an original dosage, plus or minus 5% of an original dosage, or plus or minus 5%-10% of an original dosage. In various embodiments, the nanoparticles maintain essentially the same structure and/or essentially the same function at physiological temperature, regardless of the temperature at which the nanoparticles were produced. Nanoparticles that maintain essentially the same structure and/or essentially the same function at temperatures elevated well over physiological temperatures are also contemplated. The ability to maintain essentially the same structure and/or essentially the same function at elevated temperatures is important for any number of reasons, including, for example and without limitation, sterilization processes. On the other hand, nanoparticles which maintain essentially the same structure and/or essentially the same function at reduced temperatures are also contemplated. For example, nanoparticles that maintain essentially the same structure and/or essentially the same function at or below freezing temperatures are contemplated for formulations that require or benefit from long term storage. In various aspects the nanoparticle of the disclosure have a melting temperature over 35° C., over 40° C., over 45° C., over 50° C., over 55° C., over 60° C., over 65° C., over 70° C., over 71° C., over 72° C., over 73° C., over 74° C., over 75° C., over 76° C., over 77° C., over 78° C., over 79° C. or over 80° C.

The nanoparticle of all aspects of the disclosure are stable at room temperature for at least 5 days, at least 6 days, at least 7 days, at least 8 days, at least 9 days, at least 10 days, at least 11 days, at least 12 days, at least 13 days or at least 14 days or more.

Nanoparticle of the disclosure are contemplated to have any of a number of different shapes. The shape of the nanoparticle is in certain aspects, a function of the method of its production. In other aspects, the nanoparticle acquires a shaped that is formed before, during or after the process of its production. In various embodiments, nanoparticles are provided that have a spheroid shape. Spheroid nanoparticles (referred to herein as nanospheres) having various sizes are contemplated, wherein, for example nanoparticles having a diameter between 0.1 micron and 0.5 micron, between 0.2 micron and 0.4 micron, between 0.25 micron and 0.375 micron, between 0.3 micron and 0.375 micron, between 0.325 micron and 0.375 micron, between 0.12 microns and 0.22 microns, between 0.13 microns and 0.22 microns, between 0.14 microns and 0.22 microns, between 0.15 microns and 0.22 microns, between 0.16 microns and 0.22 microns, between 0.17 microns and 0.22 microns, between 0.18 microns and 0.22 microns, between 0.19 microns and 0.22 microns, between 0.20 microns and 0.22 microns, between 0.21 microns and 0.22 microns, between 0.12 microns and 0.21 microns, between 0.12 microns and 0.20 microns, between 0.12 microns and 0.19 microns, between 0.12 microns and 0.18 microns, between 0.12 microns and 0.17 microns, between 0.12 microns and 0.16 microns, between 0.12 microns and 0.15 microns, between 0.12 microns and 0.14 microns, or between 0.12 microns and 0.13 microns are contemplated. In various aspect, nanoparticles are contemplated having a diameter of 0.01 microns to 1.0 micron, 0.05 microns to 1.0 micron, 0.05 microns to 0.95 microns, 0.05 microns to 0.9 microns, 0.05 microns to 0.85 microns, 0.05 microns to 0.8 microns, 0.05 microns to 0.75 microns, 0.05 microns to 0.7 microns, 0.05 microns to 0.65 microns, 0.05 microns to 0.6 microns, 0.05 microns to 0.55 microns, 0.05 microns to 0.5 microns, 0.1 microns to 1 micron, 0.15 microns to 1.0 microns, 0.2 microns to 1 micron, 0.25 microns to 1.0 microns, 0.3 microns to 1 micron, 0.35 microns to 1.0 microns, 0.4 microns to 1 micron, 0.45 microns to 1.0 microns, or 0.5 microns to 1 micron. In compositions of nanoparticles provided by the disclosure, the spherical nanoparticles are homogenous in that that all have the same diameter, or they are heterogeneous in that at least two nanoparticles in the composition have different diameters.

Nanoparticle are also provided which are non-spheroid. Other nanoparticles include those having a rod, fiber or whisker shape. In rod, fiber or whisker embodiments, the nanoparticle has a sufficiently high aspect ratio to avoid, slow or reduce the rate of clearance from circulation.

Aspect ratio is a term understood in the art, a high aspect ratio indicates a long and narrow shape and a low aspect ratio indicates a short and thick shape.

Nanoparticle of the disclosure are contemplated with an aspect ratio length to width of at least 3, of at least 3.5, of at least 4.0, of at least 4.5, of at least 5.0, of at least 5.5, of at least 6.0, of at least 6.5, of at least 7.0, of at least 7.5, of at least 8.0, of at least 8.5, of at least 9.0, of at least 9.5, of at least 10.0 or more. In a composition of nanoparticles contemplated, the nanoparticles have, in one embodiment, identical aspect ratios, and in alternative embodiments, at least two nanoparticles in the composition have different aspects ratios. Composition of nanoparticles are also characterized by having, on average, essentially the same aspect ratio. "Essentially the same" as used in this instance indicated that variation in aspect ratio of about 10%, about 9%, about 8%, about 7% about 6% or up to about 5% is embraced. In still other aspects, a composition of nanoparticles is provided wherein the nanoparticles in the composition have an aspect ratio of between about 1% and 200%, between about 1% and 150%, between about 1% and 100%, between about 1% and about 50%, between about 50% and 200%, between about 100% and 200%, and between about 150% and 200%. Alternatively, the nanoparticles in the composition have an aspect ratio from about X % to Y %, wherein X from 1 up to 100 and Y is from 100 up to 200.

The disclosure also provides a plurality of nanoparticles. In compositions comprising a plurality of spherical nanoparticles provided by the disclosure, nanoparticles in the plurality have an average diameter between 0.1 micron and 0.5 micron, between 0.2 micron and 0.4 micron, between 0.25 micron and 0.375 micron, between 0.3 micron and 0.375 micron, between 0.325 micron and 0.375 micron, about 0.12 micron, about 0.13 micron, about 0.14 micron, about 0.15 micron, about 0.16 micron, about 0.17 micron, about 0.18 micron, about 0.19 micron, about 0.20 micron, about 0.21 micron, about 0.22 micron, about 0.23 micron, about 0.24 micron, about 0.25 micron, about 0.26 micron, about 0.27 micron, about 0.28 micron, about 0.29 micron, about 0.30 micron, about 0.31 micron, about 0.32 micron, about 0.33 micron, about 0.34 micron, about 0.35 micron, about 0.36 micron, about 0.37 micron, about 0.38 micron, about 0.39 micron, about 0.40 micron, about 0.41 micron, about 0.42 micron, about 0.43 micron, about 0.44 micron, about 0.45 micron, about 0.46 micron, about 0.47 micron, about 0.48 micron, about 0.49 micron, about 0.50 micron, about 0.41 micron, about 0.52 micron, about 0.53 micron, about 0.54 micron, about 0.55 micron, about 0.56 micron, about 0.57 micron, about 0.58 micron, about 0.59 micron, about 0.60 micron, about 0.61 micron, about 0.62 micron, about 0.63 micron, about 0.64 micron, about 0.65 micron, about 0.66 micron, about 0.67 micron, about 0.68 micron, about 0.69 micron, about 0.70 micron, about 0.71 micron, about 0.72 micron, about 0.73 micron, about 0.74 micron, about 0.75 micron, about 0.76 micron, about 0.77 micron, about 0.78 micron, about 0.79 micron, about 0.80 micron, about 0.81 micron, about 0.82 micron, about 0.83 micron, about 0.84 micron, about 0.85 micron, about 0.86 micron, about 0.87 micron, about 0.88 micron, about 0.89 micron, about 0.90 micron, about 0.91 micron, about 0.92 micron, about 0.93 micron, about 0.94 micron, about 0.95 micron, about 0.96 micron, about 0.97 micron, about 0.98 micron, about 0.99 micron, about 1.0 micron, or more.

In various aspects, the plurality of spherical nanoparticles are characterized in that greater than 75%, greater than 80%, greater than 85%, greater than 90%, greater than 95%, greater than 96%, greater than 97%, greater than 98%, or greater than 99% of all nanoparticles have a diameter between 0.1 micron and 0.5 micron, between 0.2 micron and 0.4 micron, between 0.25 micron and 0.375 micron, between 0.3 micron and 0.375 micron, between 0.325 micron and 0.375 micron, between 0.12 microns and 0.22 microns, between 0.13 microns and 0.22 microns, between 0.14 microns and 0.22 microns, between 0.15 microns and 0.22 microns, between 0.16 microns and 0.22 microns, between 0.17 microns and 0.22 microns, between 0.18 microns and 0.22 microns, between 0.19 microns and 0.22 microns, between 0.20 microns and 0.22 microns, between 0.21 microns and 0.22 microns, between 0.12 microns and 0.21 microns, between 0.12 microns and 0.20 microns, between 0.12 microns and 0.19 microns, between 0.12 microns and 0.18 microns, between 0.12 microns and 0.17 microns, between 0.12 microns and 0.16 microns, between 0.12 microns and 0.15 microns, between 0.12 microns and 0.14 microns, between 0.12 microns and 0.13 microns, 0.01 microns to 1.0 micron, 0.05 microns to 1.0 micron, 0.05 microns to 0.95 microns, 0.05 microns to 0.9 microns, 0.05 microns to 0.85 microns, 0.05 microns to 0.8 microns, 0.05 microns to 0.75 microns, 0.05 microns to 0.7 microns, 0.05 microns to 0.65 microns, 0.05 microns to 0.6 microns, 0.05 microns to 0.55 microns, 0.05 microns to 0.5 microns, 0.1 microns to 1 micron, 0.15 microns to 1.0 microns, 0.2 microns to 1 micron, 0.25 microns to 1.0 microns, 0.3 microns to 1 micron, 0.35 microns to 1.0 microns, 0.4 microns to 1 micron, 0.45 microns to 1.0 microns, or 0.5 microns to 1 micron.

The nanoparticles in the compositions of the invention are neutrally charged such a nanoparticles having a zeta potential of about −3.0 mV to about 3.0 mV. For example, the nanoparticles have a zeta potential ranging from −3.0 mV to about 2.9 mV, about −3.0 mV to about 2.7 mV, −3.0 mV to about 2.5 mV, about −3.0 mV to about 2.3 mV, about −3.0 mV to about 2.0 mV, about −3.0 mV to about 1.7 mV, about −3.0 mV to about 1.5 mV, −3.0 mV to about 1.3 mV, about −3.0 mV to about 1.0 mV, about −3.0 mV to about 0.75 mV, about −3.0 mV to about 0.5 mV, about −3.0 mV to about 0.25 mV, about −3.0 mV to about 0.1 mV, about −3.0 mV to about 0.05 mV, about −3.0 mV to about 0.125 mV, about −3.0 mV to about 0 mV, about −3.0 mV to about −0.125, about −3.0 mV to about −0.25 mV, about −3.0 to about −0.50 mV, about −3.0 mV to about −0.75, about −3.0 mV to about −1.0 mV, about −3.0 mV to about −1.3 mV, about −3.0 mV to about −1.5 mV, about −3.0 mV to about −1.7 mV, about −3.0 mV to about −2.0 mV, about −3.0 mV to about −2.3 mV, −3.0 mV to about −2.7 mV, −3.0 mV to about 3 mV, −2.5 to about 3.0 mV, −2.5 mV to about 2.9 mV, −2.5 mV to about 2.7 mV, −2.5 mV to about 2.5 mV, about −2.5 mV to about −2.5 mV, about −2.5 mV to about 2.0 mV, about −2.5 mV to about 1.7 mV, about −2.5 mV to about 1.5 mV, −2.5 mV to about 1.3 mV, about −2.5 mV to about 1.0 mV, about −2.5 mV to about 0.75 mV, about −2.5 mV to about 0.5 mV, about −2.5 mV to about 0.25 mV, about −2.5 mV to about 0.1 mV, about −2.5 mV to about 0.05 mV, about −2.5 mV to about 0.125 mV, about −2.5 mV to about 0 mV, about −2.5 mV to about −0.125, about −2.5 mV to about −0.25 mV, about −2.5 to about −0.50 mV, about −2.5 mV to about −0.75, about −2.5 mV to about −1.0 mV, about −2.5 mV to about −1.3 mV, about −2.5 mV to about −1.5 mV, about −2.5 mV to about −1.7 mV, about −2.5 mV to about −2.0 mV, about −2.5 mV to about −2.3 mV, −2.0 to about 3.0 mV, −2.0 mV to about 2.9 mV, about −2.0 mV to about 2.7 mV, −2.0 mV to about 2.0 mV, about −2.5 mV to about 2.5 mV, about −2.0 mV to about 2.0 mV, about −2.0 mV to about 1.7 mV, about −2.0 mV to about 1.5 mV, −2.0 mV to about 1.3 mV, about −2.0 mV to about 1.0 mV, about −2.0 mV to about 0.75 mV, about −2.0 mV to about 0.5 mV, about −2.0 mV to about 0.25 mV, about −2.0 mV to about 0.1 mV, about −2.0 mV to about 0.05 mV, about −2.0 mV to about 0.125 mV, about −2.0 mV to about 0 mV, about −2.0 mV to about −0.125, about −2.0 mV to about −0.25 mV, about −2.0 to about −0.50 mV, about −2.0 mV to about −0.75, about −2.0 mV to about −1.0 mV, about −2.0 mV to about −1.3 mV, about −2.0 mV to about −1.5 mV, about −2.0 mV to about −1.7 mV, about −1.5 to about 3.0 mV, −1.5 mV to about 2.9 mV, about −1.5 mV to about 2.7 mV, −1.5 mV to about 2.5 mV, about −1.5 mV to about 2.5 mV, about −1.5 mV to about 2.0 mV, about −1.5 mV to about 1.7 mV, about −1.5 mV to about 1.5 mV, −1.5 mV to about 1.3 mV, about −1.5 mV to about 1.0 mV, about −1.5 mV to about 0.75 mV, about −1.5 mV to about 0.5 mV, about −1.5 mV to about 0.25 mV, about −1.5 mV to about 0.1 mV, about −1.5 mV to about 0.05 mV, about −2.5 mV to about 0.125 mV, about −1.5 mV to about 0 mV, about −1.5 mV to about −0.125 mV, about −0.25 mV, −1.5 to about −0.50 mV, about −1.5 mV to about −0.75, about −0.5 mV to about −1.0 mV, about −1.5 mV to about −1.3 mV, −1.0 to about 3.0 mV, −1.0 mV to about 2.9 mV, about −1.0 mV to about 2.7 mV, −1.0 mV to about 2.5 mV, about −1.0 mV to about 2.5 mV, about −1.0 mV to about 2.0 mV, about −1.0 mV to about 1.7 mV, about −1.0 mV to about 1.5 mV, −1.0 mV to about 1.3 mV, about −1.0 mV to about 1.0 mV, about −1.0 mV to about 0.75 mV, about −1.0 mV to about 0.5 mV, about −1.0 mV to about 0.25 mV, about −1.0 mV to about 0.1 mV, about −1.0 mV to about 0.05 mV, about −1.0 mV to about 0.125 mV, about −1.0 mV to about 0 mV, about −1.0 mV to about −0.125, about −1.0 mV to about −0.25 mV, about −1.0 to about −0.50 mV, about −1.0 mV to about −0.75, about −1.0 mV to about −1.0 mV, −0.5 mV to about 3.0 mV, −0.5 mV to about 2.9 mV, about −0.5 mV to about 2.7 mV, −0.5 mV to about 2.5 mV, about −0.5 mV to about 2.5 mV, about −0.5 mV to about 2.0 mV, about −0.5 mV to about 1.7 mV, about −0.5 mV to about 1.5 mV, −0.5 mV to about 1.3 mV, about −0.5 mV to about 1.0 mV, about −0.5 mV to about 0.75 mV, about −0.5 mV to about 0.5 mV, about −0.5 mV to about 0.25 mV, about −0.5 mV to about 0.1 mV, about −0.5 mV to about 0.05 mV, about −0.5 mV to about 0.125 mV, about −0.5 mV to about 0 mV, about −0.5 mV to about −0.125, about −0.5 mV to about −0.25 mV, 0 mV to about 3.0 mV, 0 mV to about 2.9 mV, about 0 mV to about 2.7 mV, 0 mV to about 2.5 mV, about 0 mV to about 2.5 mV, about 0 mV to about 2.0 mV, about 0 mV to about 1.7 mV, about 0 mV to about 1.5 mV, 0 mV to about 1.3 mV, about 0 mV to about 1.0 mV, about 0 mV to about 0.75 mV, about 0 mV to about 0.5 mV, about 0 mV to about 0.25 mV, about 0 mV to about 0.1 mV, about 0 mV to about 0.05 mV, about 0 mV to about 0.125 mV, 0.25 mV to about 3.0 mV, 0.25 mV to about 2.9 mV, about 0.25 mV to about 2.7 mV, 0.25 mV to about 2.5 mV, about 0.25 mV to about 2.5 mV, 0.25 mV to about 2.0 mV, about 0.25 mV to about 1.7 mV, about 0.25 mV to about 1.5 mV, 0.25 mV to about 1.3 mV, about 0.25 mV to about 1.0 mV, about 0.25 mV to about 0.75 mV, about 0.25 mV to about 0.5 mV, 0.5 mV to about 3.0 mV, 0.5 mV to about 2.9 mV, about 0.5 mV to about 2.7 mV, about 0.5 mV to about 2.5 mV, about 0.5 mV to about 2.5 mV, about 0.5 mV to about 2.0 mV, about 0.5 mV to about 1.7 mV, about 0.5 mV to about 1.5 mV, 0.5 mV to about 1.3 mV, about 0.5 mV to about 1.0 mV, about 0.5 mV to about 0.75 mV, 0.75 mV to about 3.0 mV, 0.75 mV to about 2.9 mV, about 0.75 mV to about 2.7 mV, 0.75 mV to about 2.5 mV, about 0.75 mV to about 2.5 mV, about 0.75 mV to about 2.0 mV, about 0.75 mV to about 1.7 mV, about 0.75 mV to about 1.5 mV, 0.75 mV to about 1.3 mV, about 0.75 mV to about 1.0 mV, 1.0 mV to about 3.0 mV, 1.0 mV to about 2.9 mV, about 1.0 mV to about 2.7 mV, 1.0 mV to about 2.5 mV, about 1.0 mV to about 2.5 mV, about 1.0 mV to about 2.0 mV, about 1.0 mV to about 1.7 mV, about 1.0 mV to about 1.5 mV, 1.0 mV to about 1.3 mV, 1.5 mV to about 3.0 mV, 1.5 mV to about 2.9 mV, about 1.5 mV to about 2.7 mV, 1.5 mV to about 2.5 mV, about 1.5 mV to about 2.5 mV, about 1.5 mV to about 2.0 mV, about 1.5 mV to about 1.7 mV, 1.7 mV to about 3.0 mV, 1.7 mV to about 2.9 mV, about 1.7 mV to about 2.7 mV, 1.7 mV to about 2.5 mV, about 1.7 mV to about 2.5 mV, about 1.7 mV to about 2.0 mV, 2.0 mV to about 3.0 mV, 2.0 mV to about 2.9 mV, about 2.0 mV to about 2.7 mV, 2.0 mV to about 2.5 mV, about 2.0 mV to about 2.5 mV, 2.5 mV to about 3.0 mV, 2.5 mV to about 2.9 mV, about 2.5 mV to about 2.7 mV, 2.7 mV to about 3.0 mV or 2.7 mV to about 2.9 mV.

The disclosure further provides nanoparticles of essentially any shape are formed using microfabrication processes well known and routinely practiced in the art. In microfabrication methods, size and shape of the nanoparticles are predetermined by design.

Core

A nanoparticle as described above is provided wherein the core is a polymer. In various aspects, the core is a crystalline polymer. "Crystalline" as used herein and understood in the art is defined to mean an arrangement of molecules in regular three dimensional arrays. In other aspects, the polymers are semi-crystalline which contain both crystalline and amorphous regions instead of all molecule arranged in regular three dimensional arrays. In various aspects, the core is a single polymer, a block copolymer, or a triblock copolymer. In specific aspects, the core comprises PLGA, PLA, PGA, (poly (ε-caprolactone) PCL, PLL, cellulose, poly (ethylene-co-vinyl acetate), polystyrene, polypropylene, dendrimer-based polymers or combinations thereof.

In various aspects, the core is biodegradable or non-biodegradable, or in a plurality of nanoparticles, combinations of biodegradable and non-biodegradable cores are formulated in contemplated. In various aspects, the core is solid, porous or hollow. In pluralities of nanoparticles, it is envisioned that mixtures of solid, porous and/or hollow cores are included.

Nanoparticle of any aspect of the disclosure include those wherein the core alternatively is a material selected from the group consisting of gold, silver, platinum, aluminum, palladium, copper, cobalt, indium, nickel, ZnS, ZnO, Ti, $TiO_2$, Sn, $SnO_2$, Si, $SiO_2$, Fe, $Fe^{+4}$, steel, cobalt-chrome alloys, Cd, CdSe, CdS, and CdS, titanium alloy, AgI, AgBr, $HgI_2$, PbS, PbSe, ZnTe, CdTe, $In_2S_3$, $In_2Se_3$, $Cd_3P_2$, $Cd_3As_2$, InAs, GaAs, cellulose or a dendrimer structure.

Hydrogel core are also provided. In one aspect, the hydrogel core provides a higher degree of temperature stable, be less likely to shear vessels and induce non-specific thrombosis and allow formation of larger nanoparticles.

Water Soluble Polymers

A nanoparticle of the disclosure is provided wherein the water soluble polymer is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly (l-hydroxymethylethylene hydroxymethylformal) (PHF), 2-methacryloyloxy-2'-ethyltrimethylammoniumphosphate (MPC), polyethylene glycol propionaldehyde, copolymers of ethylene glycol/propylene glycol, monomethoxy-polyethylene glycol, carboxymethylcellulose, polyacetals, poly-1, 3-dioxolane, poly-1,3,6-trioxane, ethylene/maleic anhydride copolymer, poly (β-amino acids) (either homopolymers or random copolymers), poly(n-vinyl pynolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and combinations or mixtures thereof. In a plurality of nanoparticles contemplated by the disclosure, each nanoparticle is contemplated, in various aspects, to have the same water soluble polymer, or alternatively, at least two nanoparticles in the plurality each have a different water soluble polymer attached thereto.

In a specific aspect, the nanoparticle of the disclosure is one wherein the water soluble polymer is PEG. For nanoparticles in this aspect, the PEG has an average molecular weight between 100 Da and 10,000 Da, 500 Da and 10,000 Da, 1000 Da and 10,000 Da, 1500 Da and 10,000 Da, 2000 Da and 10,000 Da, 2500 Da and 10,000 Da, 3000 Da and 10,000 Da, 3500 Da and 10,000 Da, 4000 Da and 10,000 Da, 4500 Da and 10,000 Da, 5000 Da and 10,000 Da, 5500 Da and 10,000 Da, 1000 Da and 9500 Da, 1000 Da and 9000 Da, 1000 Da and 8500 Da, 1000 Da and 8000 Da, 1000 Da and 7500 Da, 1000 Da and 7000 Da, 1000 Da and 6500 Da, or 1000 Da and 6000 Da. Alternatively, the nanoparticle is one in which PEG has an average molecular weight of about 100, Da, 200 Da, 300 Da, 400 Da, 1000 Da, 1500 Da, 3000 Da, 3350 Da, 4000 Da, 4600 Da, 5,000 Da, 8,000 Da, or 10,000 Da. In a plurality of nanoparticles, it is contemplated that each nanoparticle is attached to a PEG water soluble polymer of the same molecular weight, or in the alternative, at least two nanoparticles in the plurality are each attached to a PEG water soluble polymer which do not have the same molecular weight.

The nanoparticle of the disclosure includes those wherein the water soluble polymer is attached to the core at a molar ratio of 0.1:1, 0.2:1, 0.3:1, 0.4:1, 0.5:1, 0.6:1, 0.7:1, 0.8:1, 0.9:1, 1:1, 1:2, 1:3, 1:4, 1:5, 1:6, 1:7, 1:8, 1:9, 1:10 or greater. In various aspect, a plurality is proved wherein the water soluble polymer to core ratio is identical for each nanoparticle in the plurality, and in alternative aspect, at least two nanoparticles in the plurality have different water soluble polymer to core ratios.

The degree to which a nanoparticle is associated with a water soluble polymer is, in various aspects, determined by the route of administration chosen.

Peptides

The nanoparticle of the disclosure is characterized by having a peptide associated therewith. In various aspects of the disclosure. The peptide is linear or cyclic. In specific embodiments, the peptide comprises a core sequence selected from the group consisting of RGD, RGDS (SEQ ID NO: 1), GRGDS (SEQ ID NO: 2), GRGDSP (SEQ ID NO: 3), GRGDSPK (SEQ ID NO: 4), GRGDN (SEQ ID NO: 5), GRGDNP (SEQ ID NO: 6), GGGGRGDS (SEQ ID NO: 7), GRGDK (SEQ ID NO: 8), GRGDTP (SEQ ID NO: 9), cRGD, YRGDS (SEQ ID NO: 10) or variants thereof. Variants are used herein include peptides have a core sequence as defined herein and one or more additional amino acid residues attached at one or both ends of the core sequence, a peptide having a core sequence as defined herein but wherein one or more amino acid residues in the core sequence is substituted with an alternative amino acid residue; the alternative amino acid residue being a naturally-occurring amino acid residue or a non-naturally-occurring amino acid residue, a peptide having a core sequence as defined herein but wherein one or more amino acid residues in the core sequence is deleted, or combinations thereof, wherein the additional amino acid residue, the amino acid substitution, the amino acid deletion or the combination of changes does (or do) not essentially alter the activity of the nanoparticle. "Essentially" as used in this aspect is the same as the meaning described elsewhere in the disclosure.

In various aspects, the RGD peptide is in a tandem repeat arrangement and in embodiments of this aspects, 1, 2, 3, 4, 5, 6, 7, 8, 9, 10 or more copies of the RGD peptide are contemplated. In another aspect, multiple copies of an RGD peptide are attached to the same nanoparticle, albeit not in a random repeat arrangement.

In various aspects wherein the nanoparticle is associated with multiple RGD peptides, the disclosure provide a nanoparticle wherein all copies of the RGD peptide are the same, as wells as aspects wherein two of the RGD peptide have different sequences.

In a plurality of nanoparticles contemplated, embodiments are provided wherein the RGD peptide (or multiple copies of RGD peptides) are identical on each nanoparticle in the plurality. In alternative aspects, at least two nanoparticles in the plurality each are associated with one or more distinct RGD peptides.

In various aspect, the number of peptides on a nanoparticle, i.e., the peptide density, affects platelet aggregation.

Poloxamers

The dry spray compositions of the invention may comprise a poloxamer which is a stabilizer. The poloxamer reduces or eliminates aggregation of the neutrally-charged nanoparticles. Poloxamers are non-ionic triblock copolymers with a hydrophobic block at the center (poly(propylene oxide)) and two PEG groups at the ends. Poloxamers are also known as Pluronics in the field. Any poloxamer or pluroinic may be used in the compositions of the invention.

For example, the invention provides for dry spray compositions wherein the poloxamer is selected from the group consisting of poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407 and Kolliphor P 188, Pluronic® 1010, Pluronic® 17R2, Pluronic® 17R, Pluronic® 25R2, Pluronic® 25R4, Pluronic® 31R1, Pluronic® F 108 Cast Solid Surfacta, Pluronic® F 108 NF, Pluronic® F 108 Pastille, Pluronic® F 108NF Prill Poloxamer 338, Pluronic® F 127, Pluronic® F 127 NF, Pluronic® F 127 NF 500 BHT Prill, Pluronic® F 127 NF Prill Poloxamer 407, Pluronic® F 38, Pluronic® F 38 Pastille, Pluronic® F 68, Pluronic® F 68 Pastille, Pluronic® F 68 LF Pastille, Pluronic® F 68 NF, Pluronic® F 68 NF Prill Poloxamer 188, Pluronic® F 77, Pluronic® F 77 Micropastille, Pluronic® F 87, Pluronic® F 87 NF, Pluronic® F 87 NF Prill Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 44 NF, Poloxamer 124, Pluronic® L 61, Pluronic® L 62, Pluronic® L 62 LF, Pluronic® L 62D, Pluronic® L 64, Pluronic® L 81, Pluronic® L 92, Pluronic® L44 NF, Pluronic® N 3, Pluronic® P 103, Pluronic® P 104, Pluronic® P 105, Pluronic® P 123 Surfactant, Pluronic® P 65, Pluronic® P 84, and Pluronic® P 85.

In addition, other triblock copolymers that have PEG on the ends and a more hydrophobic middle group may be used as a stabilizer in the compositions as long as the polymer is soluble in water. Exemplary triblock copolymers include polymers having the ABA structure where A is PEG or PVA or another water soluble polymer and B is PLA, PGA, PLGA, polypropylene, poly(propylene oxide), a polyamide, polystyrene, polybutadine, are examples. Alternatively, the triblock copolymer having the ABA structure where B is PEG or any of the water soluble polymers and A is any of the hydrophobic or water insoluble polymers.

The dry spray compositions of the invention may comprise about 0.1% poloxamer, about 0.2% poloxamer, about 0.3% poloxamer, about 0.4% poloxamer, about 0.5% poloxamer, about 0.6% poloxamer, about 0.7% poloxamer, about 0.8% poloxamer, about 0.9% poloxamer, about 1% poloxamer, about 2% poloxamer, about 3% poloxamer, about 4% poloxamer, about 5% poloxamer, about 6% poloxamer, about 7% poloxamer, about 8% poloxamer, about 9% poloxamer, about 10% poloxamer, about 11% poloxamer, about 12% poloxamer, about 13% poloxamer, about 14% poloxamer, about 15% poloxamer, about 16% poloxamer, about 17% poloxamer, about 18% poloxamer, about 19% poloxamer, about 20% poloxamer, about 21% poloxamer, about 22% poloxamer, about 23% poloxamer, about 24% poloxamer, about 25% poloxamer, about 26% poloxamer, about 27% poloxamer, about 28% poloxamer, about 29% poloxamer, about 30% poloxamer, about 31% poloxamer, about 32% poloxamer, about 33% poloxamer, about 34% poloxamer, about 35% poloxamer, about 36% poloxamer, about 37% poloxamer, about 38% poloxamer, about 39% poloxamer, about 40% poloxamer, about 41% poloxamer, about 42% poloxamer, about 43% poloxamer, about 44% poloxamer, about 45% poloxamer, about 46% poloxamer, about 47% poloxamer, about 48% poloxamer, about 49% poloxamer, about 40% poloxamer, about 51% poloxamer, about 52% poloxamer, about 53% poloxamer, about 54% poloxamer, about 55% poloxamer, about 56% poloxamer, about 57% poloxamer, about 58% poloxamer, about 59% poloxamer or about 60% poloxamer.

The invention provides for dry spray composition wherein the poloxamer is present at about 0.1% to about 60% of the composition, or at about 0.1% to about 55% of the composition, or at about 0.1% to about 50% of the composition, or at about 0.1% to about 45% of the composition, or at about 0.1% to about 40% of the composition, or at about 0.1% to about 35% of the composition, or at about 0.1% to about 30% of the composition, or at about 0.1% to about 25% of the composition, or at about 0.1% to about 20% of the composition, or at about 0.1% to about 15% of the composition, or at about 0.1% to about 12% of the composition, or at about 0.1% to about 10% of the composition, or at about 0.1% to about 5% of the composition, or at about 0.1% to about 1% of the composition, or at about 0.1% to about 0.5% of the composition, about 0.5% to about 60% of the composition, or at about 0.5% to about 55% of the composition, or at about 0.5% to about 50% of the composition, or at about 0.5% to about 45% of the composition, or at about 0.1% to about 40% of the composition, or at about 0.5% to about 35% of the composition, or at about 0.5% to about 30% of the composition, or at about 0.5% to about 25% of the composition, or at about 0.5% to about 20% of the composition, or at about 0.5% to about 15% of the composition, or at about 0.5% to about 12% of the composition, or at about 0.5% to about 10% of the composition, or at about 0.5% to about 5% of the composition, or at about 0.5% to about 1% of the composition, or about 1% to about 60% of the composition, or at about 1% to about 55% of the composition, or at about 1% to about 50% of the composition, or at about 1% to about 45% of the composition, or at about 1% to about 40% of the composition, or at about 1% to about 35% of the composition, or at about 1% to about 30% of the composition, or at about 1% to about 25% of the composition, or at about 1% to about 20% of the composition, or at about 1% to about 15% of the composition, or at about 1% to about 12% of the composition, or at about 1% to about 10% of the composition, or at about 1% to about 5% of the composition, or about 5% to about 60% of the composition, or at about 5% to about 55% of the composition, or at about 5% to about 50% of the composition, or at about 5% to about 45% of the composition, or at about 5% to about 40% of the composition, or at about 5% to about 35% of the composition, or at about 5% to about 30% of the composition, or at about 5% to about 25% of the composition, or at about 5% to about 20% of the composition, or at about 5% to about 15% of the composition, or at about 5% to about 12% of the composition, or at about 5% to about 10% of the composition, or about 10% to about 60%, or at about 10% to about 50% of the composition, or at about 10% to about 45% of the composition, or at about 10% to about 40% of the composition, or at about 10% to about 35% of the composition, or at about 10% to about 30% of the composition, or at about 10% to about 25% of the composition, or at about 10% to about 20% of the composition, or at about 10% to about 15% of the composition, or at about 10% to about 12% of the composition, or about 20% to about 60% of the composition, or at about 20% to about 50% of the composition, or at about 20% to about 45% of the composition, or at about 20% to about 40% of the composition, or at about 20% to about 35% of the composition, or at about 20% to about 30% of the composition, or at about 20% to about 25% of the composition, or about 30% to about 60%, or at about 30% to about 50% of the composition, or at about 30% to about 45% of the composition, or at about 30% to about 40% of the composition, or at about 30% to about 35% of the composition, or about 40% to about 60%, or at about 40% to about 50% of the composition, or at about 40% to about 45% of the composition, or about 45% to about 60%, or at about 45% to about 50% of the composition, or at about 50% to about 60% of the composition.

The invention provides for dry spray composition wherein the poloxamer is present up to 50 times nanoparticle mass, or up to 40 times nanoparticle mass, or up to 35 time nanoparticle mass, or up to 30 times nanoparticle mass, or up to 25 times nanoparticle mass, or up to 20 times nanoparticle mass, or up to 15 times nanoparticle mass, or up to 10 times nanoparticle mass, or up to 9 times nanoparticle mass, or up to 8 times nanoparticle mass, or up to 7 times nanoparticle mass, or up to 6 times nanoparticle mass, or up to 5 times nanoparticle mass.

Other stabilizers which do not impart a negative charge on the dry spray composition may be used in the compositions of the invention, such as poly(acrylic acid), poloxamer such as poloxamer 188 or PEG.

Other Compounds with the Nanoparticle

A nanoparticle of the disclosure is also contemplated further comprising a therapeutic compound. In various aspects, the therapeutic compound is hydrophobic and in still other aspects, the therapeutic compound is hydrophilic. A nanoparticle of the disclosure is provided wherein the therapeutic compound is covalently attached to the nanoparticle, non-covalently associated with the nanoparticle, associated with the nanoparticle through electrostatic interaction, or associated with the nanoparticle through hydrophobic interaction. In various embodiments, the therapeutic compound is a growth factor, a cytokine, a steroid, or a small molecule. Embodiments are contemplated wherein more than one therapeutic compound is associated with a nanoparticle. In this aspect, each therapeutic compounds associated with the nanoparticle is the same, or each therapeutic compound associated with the nanoparticle is different. In a plurality of nanoparticles provided by the disclosure, each nanoparticle in the plurality is associated with the same therapeutic compound or compounds, or in the alternative, at least two nanoparticles in the plurality is each associated with one or more different therapeutic compounds.

In various aspects, the therapeutic compound is a anticancer compound, and in specific embodiments, the therapeutic compound is selected from the group consisting of: an alkylating agents including without limitation nitrogen mustards, such as mechlor-ethamine, cyclophosphamide, ifosfamide, melphalan and chlorambucil; nitrosoureas, such as without limitation carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as without limitation busulfan; triazines such as dacarbazine (DTIC); antimetabolites including folic acid analogs such as methotrexate and trimetrexate; pyrimidine analogs such as without limitation 5-fluorouracil, fluorodeoxyuridine, gemcitabine, cytosine arabinoside (AraC, cytarabine), 5-azacytidine, 2,2'-difluorodeoxycytidine; purine analogs such as without limitation 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (clathibine, 2-CdA); natural products including without limitation antimitotic drugs such as paclitaxel; vinca alkaloids including without limitation vinblastine (VLB), vincristine, and vinorelbine, taxotere, estramustine, and estramustine phosphate; epipodophylotoxins such as without limitation etoposide and teniposide; antibiotics such as without limitation actimomycin D, daunomycin (rubidomycin), doxorubicin, mitoxantrone, idarubicin, bleomycins, plicamycin (mithramycin), mitomycinC, and actinomycin; enzymes such as without limitation L-asparaginase; biological response modifiers such as without limitation interferon-alpha, IL-2, G-CSF and GM-CSF; miscellaneous agents including without limitation platinum coordination complexes such as cisplatin and carboplatin; anthracenediones such as without limitation mitoxantrone; substituted urea such as without limitation hydroxyurea; methylhydrazine derivatives including without limitation N-methylhydrazine (MIH) and procarbazine; adrenocortical suppressants such as without limitation mitotane (o,p'-DDD) and aminoglutethimide; hormones and antagonists including without limitation adrenocorticosteroid antagonists such as prednisone and equivalents, dexamethasone and aminoglutethimide; progestin such as without limitation hydroxyprogesterone caproate, medroxyprogesterone acetate and megestrol acetate; estrogen such as without limitation diethylstilbestrol and ethinyl estradiol equivalents; antiestrogen such as without limitation tamoxifen; androgens including testosterone propionate and fluoxymesterone/equivalents; antiandrogens such as without limitation flutamide, gonadotropin-releasing hormone analogs and leuprolide; non-steroidal antiandrogens such as without limitation flutamide; folate inhibitors; tyrosine kinase inhibitors such as without limitation AG1478, and radiosensitizing compounds.

In various aspects, the therapeutic compound is selected from the group consisting of AG1478, acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, droloxifene, dromostanolone, duazomycin, edatrexate, eflomithine, elsamitrucin, enloplatin, enpromate, epipropidine, epirubicin, erbulozole, esorubicin, estramustine, estramustine, etanidazole, etoposide, etoposide, etoprine, fadrozole, fazarabine, fenretinide, floxuridine, fludarabine, fluorouracil, flurocitabine, fosquidone, fostriecin, fulvestrant, gemcitabine, gemcitabine, hydroxyurea, idarubicin, ifosfamide, ilmofosine, interleukin II (IL-2, including recombinant interleukin II or rIL2), interferon alpha-2a, interferon alpha-2b, interferon alpha-n1, interferon alpha-n3, interferon beta-1a, interferon gamma-I b, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, methotrexate, metoprine, meturedepa, mitindomide, mitocarcin, mitocromin, mitogillin, mitomalcin, mitomycin, nitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, puromycin, pyrazofurin, riboprine, rogletimide, safingol, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, triethylenemelamine, trimetrexate, triptorelin, tubulozole, uracil mustard, uredepa, vapreotide, verteporlin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin. These and other antineoplastic therapeutic agents are described, for example, in Goodman & Gilman's The Pharmacological Basis of Therapeutics, McGraw-Hill Professional, 10th ed., 2001.

In various aspects, the therapeutic compound is an anti-inflammatory selected from the group consisting of glucocorticoids; kallikrein inhibitors; corticosteroids (e.g. without limitation, prednisone, methylprednisolone, dexamethasone, or triamcinalone acetinide); anti-inflammatory agents (such as without limitation noncorticosteroid anti-inflammatory compounds (e.g., without limitation ibuprofen or flubiproben)); vitamins and minerals (e.g., without limitation zinc); anti-oxidants (e.g., without limitation carotenoids (such as without limitation a xanthophyll carotenoid like zeaxanthin or lutein)) and agents that inhibit tumor necrosis factor (TNF) activity, such as without limitation adalimumab (HUMIRA®), infliximab REMICADE®), certolizumab (CIMZIA®), golimumab (SIMPONI®), and etanercept (ENBREL®).

In various aspects, the therapeutic compound is M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors for use herein include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor ÿ, cytokine-induced eutrophils chemotactic factor 1, cytokine-induced eutrophils, chemotactic factor 2, cytokine-induced neutrophils chemotactic factor 2, endothelial cell growth factor, endothelin 1, epithelial-derived eutrophils attractant, glial cell line-derived neutrophic factor receptor 1, glial cell line-derived neutrophic factor receptor 2, growth related protein, growth related protein, growth related protein ÿ, growth related protein, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, pre-B cell growth stimulating factor, stem cell factor, stem cell factor receptor, transforming growth factor, transforming growth factor, transforming growth factor, transforming growth factor 2, transforming growth factor ÿ, transforming growth factor, transforming growth factor β, latent transforming growth factor β, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, intracellular sigma peptide (ISP), and chimeric proteins and biologically or immunologically active fragments thereof.

Methods are also provided for with anticoagulation drugs. Including, for example and without limitation, plavix, aspirin, warfarin, heparin, ticlopidine, enoxaparin, Coumadin, dicumarol, acenocoumarol, citric acid, lepirudin and combinations thereof.

Methods in this aspect overcome the effects of these anticoagulant drugs which would be extremely helpful in surgery.

Spray Compositions

The dry spray compositions of the invention may be administered as a dry powder. The dry spray composition may be produced by spray drying which is a method of producing a dry powder from a liquid or a dispersion in a liquid by rapidly drying with a hot gas. The powder may also be prepared by spray-freeze drying.

The dry spray compositions of the invention may be administered using a spray system, an air brush system or a syringe type system. Alternatively, the compositions may be administered to the subject using an endoscope or other laproscopic device. Finally, the compositions of the invention may be administered via catheter. For example, the air brush system has broad applications including: administering the synthetic platelets to functional injuries such as groin injuries in which the bleeding cannot be controls with typical pressure dressings, GI bleeds, and bleeding following trauma such as gross blunt trauma associated bleeds (e.g liver lacerations, other major organ lacerations.)

The spray dispenser of the invention includes any device that releases a dry aerosol, dry mist or fry film at the site of injury to efficiently reduce bleeding. Any device designed to produce a fine spray of powder or particles that can be suspended in a gas such as the atmosphere may be used to administer the spray composition. For example, the spray composition of the invention may be administered by an atomizer, pump, sprayer or dropper.

Optionally, the spray compositions of the invention are formulated to be dispensed as a dry aerosol. The aerosol dispenser is preferably a conventional aerosol having a conventional atomizer or metered spray aerosol valve. For example, the pump dispenser is preferably a conventional can or bottle having a conventional metered spray pump.

Preferably, the aerosol dispenser has an all position valve having a covering that permits spraying when the dispenser is held at any angle. In this way, horizontal bottom surfaces, as well as horizontal top surfaces and vertical surfaces, can be sprayed. The valve actuator can be any actuator which produces a spray at the nozzle.

A preferred valve actuator is a mechanical breakup actuator, which employs mechanical forces rather than expansion and evaporation of the propellant to produce a spray. A typical mechanical breakup actuator has a conical or cylindrical swirl chamber with an inlet channel oriented perpendicular to the axis thereof. This structure imparts a swirling motion to the aerosol mixture upon discharge. The swirling motion occurs around the axis of the swirl chamber forming a thin conical film of discharged mixture, which breaks into droplets as it leaves the swirl chamber and travels in the direction of the axis thereof. The result is a fine, soft, dispersed spray which can be easily controlled to produce a stable thin film of even thickness completely contacting the application site. In dispensing a spray composition of the invention, the dispenser is typically held about 1 to 5 inches (2.5 to 12.5 cm) from the application site and produces a film of even thickness. The dispensers used in the present invention are preferably compact units, which can be conveniently used for quick and easy application of the composition over a large surface area.

Pharmaceutical Compositions

The invention provides for pharmaceutical dry spray compositions comprising a polymer or nanoparticle of the invention. In various aspects, the pharmaceutical dry spray composition is a unit dose formulation. In various aspects the pharmaceutical dry spray composition further comprises polyacrylic acid, poloxamer 188 or PEG.

The compositions of the invention may be formulated for administration using a spray-on system. In one exemplary spray system, the nanoparticles within the composition may or may not be suspended or dissolved in a carrier such as water. In another spray system, The nanoparticles within the compositions are suspended or dissolved at various ratios in a water miscible such as DMSO, NMP, dimethylformamide (DMF) or tetrahydrofuran (THF). The compositions are then administered directly on the internal or external site of injury using a spray system, a brush system or syringe-type system. The spray system may be an aerosol spray or electrostatic spray. Alternatively, these compositions may be introduced to the injury using an endoscopic or other laproscopic device.

The disclosure provides pharmaceutical dry spray compositions formulated for delivery of nanoparticles at 1 mg/kg to 1 g/kg, 10 mg/kg to 1 g/kg, 20 mg/kg to 1 g/kg, 30 mg/kg to 1 g/kg, 40 mg/kg to 1 g/kg, 50 mg/kg to 1 g/kg, 60 mg/kg to 1 g/kg, 70 mg/kg to 1 g/kg, 80 mg/kg to 1 g/kg, 90 mg/kg to 1 g/kg, 10 mg/kg to 900 mg/kg, 10 mg/kg to 800 m/kg, 10 mg/kg to 700 mg/kg, 10 mg/kg to 600 mg/kg, 10 mg/kg to 500 mg/kg, 10 mg/kg to 400 mg/kg, 10 mg/kg to 300 mg/kg, 10 mg/kg to 200 mg/kg, 10 mg/kg to 100 mg/kg, 10 mg/kg to 75 mg/kg, 10 mg/kg to 50 mg/kg, 50 mg/kg to 900 mg/kg, 100 mg/kg to 800 mg/kg, 200 mg/kg to 700 mg/kg, 300 mg/kg to 600 mg/kg, 400 mg/kg to 500 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, or more.

Single dose administrations are provided, as well as multiple dose administrations. Multiple dose administration includes those wherein a second dose is administered within minutes, hours, day, weeks, or months after an initial administration.

Uses of the Compositions

A method of treating a condition in an individual is provided comprising the step of administering the spray compositions of the disclosure to a patient in need thereof in an amount effective to treat the condition. In various aspects, the individual has a bleeding disorder. Methods are provided wherein the spray composition is administered in an amount effective to reduce bleeding time by more than 15%, by more than 20%, by more than 25%, or by more than 30% compared to no administration or administration of saline. In various aspects, the method is used wherein the bleeding disorder is a symptom of a clotting disorder, an acquired platelet function defect, a congenital platelet function defect, a congenital protein C or S deficiency, disseminated intravascular coagulation (DIC), Factor II deficiency, Factor V deficiency, Factor VII deficiency, Factor X deficiency, Factor XII deficiency, Hemophilia A, Hemophilia B, Idiopathic thrombocytopenic purpura (ITP), von Willebrand's disease (types I, II, and III), megakaryocyte/platelet deficiency. In various aspects, a method is provided wherein the condition is thrombocytopenia arising from chemotherapy and other therapy with a variety of drugs, radiation therapy, surgery, accidental blood loss, and other specific disease conditions. In various aspects, a method is provided wherein the condition is aplastic anemia, idiopathic or immune thrombocytopenia (ITP), including idiopathic thrombocytopenic purpura associated with breast cancer metastatic tumors which result in thrombocytopenia, systemic lupus erythematosus, including neonatal lupus syndrome, metastatic tumors which result in thrombocytopenia, splenomegaly, Fanconi's syndrome, vitamin B12 deficiency, folic acid deficiency, May-Hegglin anomaly, Wiskott-Aldrich syndrome, paroxysmal nocturnal hemoglobinuria, HIV associated ITP and HIV-related thrombotic thrombocytopenic purpura; chronic liver disease; myelodysplastic syndrome associated with thrombocytopenia; paroxysmal nocturnal hemoglobinuria, acute profound thrombocytopenia following C7E3 Fab (Abciximab) therapy; alloimmune thrombocytopenia, including maternal alloimmune thrombocytopenia; thrombocytopenia associated with antiphospholipid antibodies and thrombosis; autoimmune thrombocytopenia; drug-induced immune thrombocytopenia, including carboplatin-induced thrombocytopenia, heparin-induced thrombocytopenia; fetal thrombocytopenia; gestational thrombocytopenia; Hughes' syndrome; lupoid thrombocytopenia; accidental and/or massive blood loss; myeloproliferative disorders; thrombocytopenia in patients with malignancies; thrombotic thrombocytopenia purpura, including thrombotic microangiopathy manifesting as thrombotic thrombocytopenic purpura/hemolytic uremic syndrome in cancer patients; autoimmune hemolytic anemia; occult jejunal diverticulum perforation; pure red cell aplasia; autoimmune thrombocytopenia; nephropathia epidemica; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes in childhood; and hematologic manifestations related to viral infection including hepatitis A virus and CMV-associated thrombocytopenia. In various aspects, a method is provided wherein the condition arises from treatment for AIDS which result in thrombocytopenia. In various aspects, the treatment for AIDS is administration of AZT.

In various aspect, the individual being treated is suffering from a wound healing disorders, trauma, blast trauma, a spinal cord injury, hemorrhagic stroke, hemorrhaging following administration of TPA, or intraventricular hemorrhaging which is seen in many conditions but especially acute in premature births.

EXAMPLES

Example 1

Nanoparticle Synthesis

Nanoparticles were synthesized from poly (lactic-co-glycolic acid)-poly$_L$-lysine (PLGA-PLL) block copolymer conjugated with polyethylene glycol (PEG) arms. Spherical nanoparticles were fabricated using a nano precipitation method as described herein. Dexamethasone was dissolved in a solvent, and the appropriate amount of polymer was also dissolved and mixed with the drug. The drug/polymer solution was pipetted dropwise into spinning 1×PBS. The resultant solution was allowed to stir uncovered for approximately 20 min at room temperature. After the nanospheres stir hardened, the pH was adjusted down to 3.0-2.7 to induce flocculation. This pH range was found to be useful for flocculation to occur. The nanospheres were purified by centrifugation (500 g, 3 min, 3×), resuspended in deionized water, frozen, and freeze-dried on a lyophilizer. A release study was performed by dissolving 10 mg of nanospheres into 1 mL 1×PBS, repeated in triplicate.

Size of the nanospheres was determined by dynamic light scattering (DLS). Conformation of size and morphology was determined by a scanning electron microscope (SEM). The amount of drug was determined by dissolving spheres in DMSO and running on a UV-Vis. Release study data was gathered at various time points and was run on UV-Vis to determine how dexamethasone elutes out of the nanoparticles over time.

Example 2

Attachment of Peptides to Nanoparticles

The yield and time to make product has been significantly reduced by determining the shortest times necessary for intermediate treatment steps. Yield is significantly increased using centrifugation to collect PLGA-PLL-PEG after precipitating. Yield is also significantly increased with nanoprecipitation nanoparticle formation method and even further increased if using the poly(acrylic acid) coacervate precipitation technique for nanoparticle collection.

Once the PLGA-PLL-PEG is synthesized, the active peptide such as GRGDS (SEQ ID NO: 2) needs to be coupled to the polymer.

When the quad block polymer (PLGA-PLL-PEG-peptide) was used, yield of spheres was extremely low. Since the peptide was the most expensive portion of the polymer, a method was employed to form spheres from the triblock (PLGA-PLL-PEG) and then attach the peptide to the spheres themselves.

Conjugation of the peptide to triblock nanoparticles led to approx. 50% conjugation efficiency (calculated as the arginine to lysine ratio).

However, it was found that an extra rinse step of the nanospheres before amino acid analysis led to significant loss of the peptide with a conjugation efficiency of 11%. Upon scaling the reaction up for a 1 g batch of nanospheres, the conjugation efficiency essentially dropped to 0%. Therefore, a method was pursued that would allow one to make the entire quad block polymer and with at least comparable yield produce nanoparticles with a tight size distribution.

This approach led to the manufacture of a quadblock polymer prior to the formation of the nanoparticle. The quadblock conjugation efficiency was approximately 80%, but dropped to 13% after nanosphere formation using the nanoprecipitation technique with and without poly(acrylic acid). Finally, the quadblock was made by reactivating the polymer with CDI in DMSO immediately prior to the addition of the peptide. This step increases the conjugation of peptide to above 50% (n=3).

Emulsion Method

The emulsion method succeeds in making spheres of diameter between 326-361 nm.

The emulsion method stir-hardens the nanospheres in 50 ml of 5% PVA in deionized water. Scaling up the production of nanospheres using this method requires large volumes of solution for stir hardening. This observation, coupled with the fact that prior methods added the peptide for the conjugation step after forming the particles, means that a very large amount of peptide would be needed for the large volume of solution to achieve a reasonable coupling efficiency.

For the nanoprecipitation method, scaled down version, stir hardening in 10 ml PBS was carried out with simultaneous conjugation of the peptide. This step adds a sufficient amount of peptide. The nanoprecipitation method also lends itself to the formation of nanoparticles with the quadblock polymer eliminating the need for a post-fabrication coupling reaction.

There are a number of fundamental issues identified with nanoparticles, including uniformity of particles, aggregation of particles, challenges in resuspending nanoparticles and challenges of resuspending following lyophilization Groups have come up with a number of approaches to deal with these challenges. For example, one can have a lyoprotectant to resuspend small nanoparticles following lyophilization. (Sauaia et al., *J. Trauma* 38: 185 (1995), Champion et al., *J. Trauma* 54: S13 (2003)). Other found that through nanoprecipitation technique coupled with the use of poly(acrylic acid) to flocculate the particles, the need to add a lyoprotectant to the solution was avoided.

Nanoprecipitation

The nanoprecipitation method uses dropwise addition of polymer dissolved in a water miscible solvent such as acetonitrile to make spheres of consistent size (Regel et al., *Acta. Anaesthesiol. Scand.* Suppl 110: 71 (1997); Lee et al., *Exp. Opin. Investig. Drugs* 9: 457 (2000); Blajchman, *Nat. Med.* 5: 17 (1999); Lee et al., *Br. J. Haematol.* 114: 496 (2001)).

Poly(Acrylic Acid) Coacervate Precipitation

This method modified from (Regel et al. (1997); Kim et al., Artif. *Cells Blood Substit. Immobil. Biotechnol.* 34: 537 (2006)) was employed to increase yield of nanoparticles and to reduce aggregation of spheres during centrifugation and lyophilization steps as had previously been observed. The precipitation allows for gentle centrifugation <500 g.

The size reproducibility has thus far been shown to be an advantage over the emulsion and nanoprecipitation alone methods which is highly dependent on sonication conditions to make a homogenous size distribution. SEM image shows morphology of nanoparticles and homogeneity of size. Histogram inlay was made from 100 measurements of nanoparticle diameter, and shows size distribution is centered around 236.1 nm+/−56.6 nm.

Method for Making PAA-Coated Nanoprecipitated Synthetic Platelets

PLGA (Resomer 503H) was purchased from Evonik Industries. Poly-1-lysine and PEG (~4600 Da MW) were purchased from Sigma Aldrich. All reagents were ACS grade and were purchased from Fisher Scientific. PLGA-PLL-PEG coblock polymer was made using standard bioconjugation techniques as previously described (Lavik et al).

Quadblock Conjugation

PLGA-PLL-PEG was dissolved in N-methyl-2-pyrrolidone (NMP) to a concentration of 100 mg/ml. Two molar equivalents of CDI were added to reactivate the PEG groups and stirred for 1 hour. Twenty five mg of oligopeptides (GRGDS (SEQ ID NO: 2) was dissolved in 1 ml NMP and added to the stirring polymer solution. This mixture was reacted for 3 hours, and then transferred to dialysis tubing (SpectraPor 2 kDa MWCO). Dialysis water was changed every half hour for 4 hours with Type I D.I. water. The product was then snap-frozen in liquid nitrogen and lyophilized for 2 days.

Nanoprecipitation

The resulting quadblock copolymer PLGA-PLL-PEG-GRGDS was then dissolved to a concentration of 20 mg/ml in acetonitrile. This solution was added dropwise to a stirring volume of PBS. The general rule is to use twice the volume of PBS as acetonitrile. Precipitated nanoparticles formed as the water-miscible solvent dissipates. However, to scale up to quantities greater than 300 mg starting quadblock, it was found that priming the precipitation volume with acetonitrile reduced the spontaneous formation of aggregates. Solvent:water ratios were adjusted throughout the precipitation process so that the final concentration in the precipitation volume is 2:1 PBS:acetonitrile. The particles were then stir-hardened for 3 hours. Particles were then collected using centrifugation @ 15000 g and rinsing with PBS 3 times. Alternatively, particles were collected using the coacervate precipitation method.

Coacervate Precipitation

One mass equivalent of dry poly(acrylic acid) was added to the stirring particle suspension. 1% w/v pAA was then added to the stirring suspension until flocculation occurs. Stirring was paused momentarily after each addition of pAA to observe flocculation. After 5 minutes, the flocculated particles were collected by centrifugation at 500 g, and rinsed 3 times with 1% pAA (centrifuging @ 500 g, 2 m, 4 C between rinses). On the final rinse, particles were resuspended with D.I. water, snap-frozen and lyophilized for 2-5 days, depending on the final volume of water.

Resuspension

Particles were massed and resuspended to a concentration of 20 mg/ml in 1×PBS. Particles are either vortexed to resuspend, or alternatively vortexed and briefly sonicated at 4 W to a total energy of 50 J using a probe sonicator (VCX-130, Sonics & Materials, Inc.).

Example 3

In Vivo Testing in the Femoral Artery Injury Model

In preliminary work, a femoral artery injury model was used. It is a very clean model that allows simple assessment of the impact of a therapy on bleeding. Male Sprague-Dawley rats were anesthetized with isoflurane. The animal's temperature was maintained using a heating pad and monitored throughout the experiment using a temperature probe. An arterial catheter was used for measuring blood pressure and blood draws, and a venous catheter was used for administration of the agent being tested. The abdominal cavity was opened, and the median lobe of the liver is cut sharply 1.3 cm from the superior vena cava following. The cavity was immediately closed, and the experimental agent was delivered.

Blood samples were drawn immediately before the injury, at 5 minutes post injury, and at 30 minutes post injury. Animals were maintained for 60 minutes or until death. At the end of 60 minutes, pre-weighed sponges were used to collect the blood in the abdominal cavity to determine blood loss. All the major organs were collected for histology and biodistribution of the nanoparticles.

Nanoparticles of the invention were intravenously administered into a canulated femoral vein in 0.5 ml injection volume (20 mg·ml), 3 minute injections with 5 minute equilibration shortly after injury. The nanoparticles administered had a PLGA-PLL nanosphere core (~200 nm), multiple 4600 kD PEG arms and one of the following RGD peptides conjugated to the PEG arms: RGD, RGDS (SEQ ID NO: 1), and GRGDS (SEQ ID NO: 2).

Figure 2A:
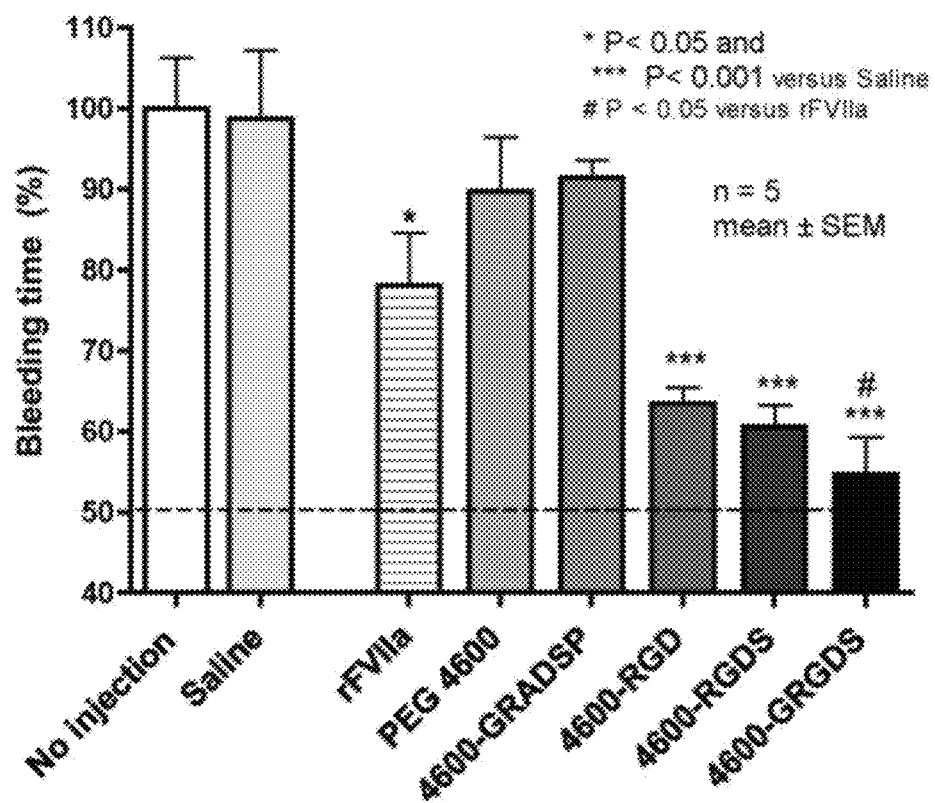
FIG. 2A-FIG. 2B depicts the effect of nanoparticles on bleeding time in vitro
Figure 2B:
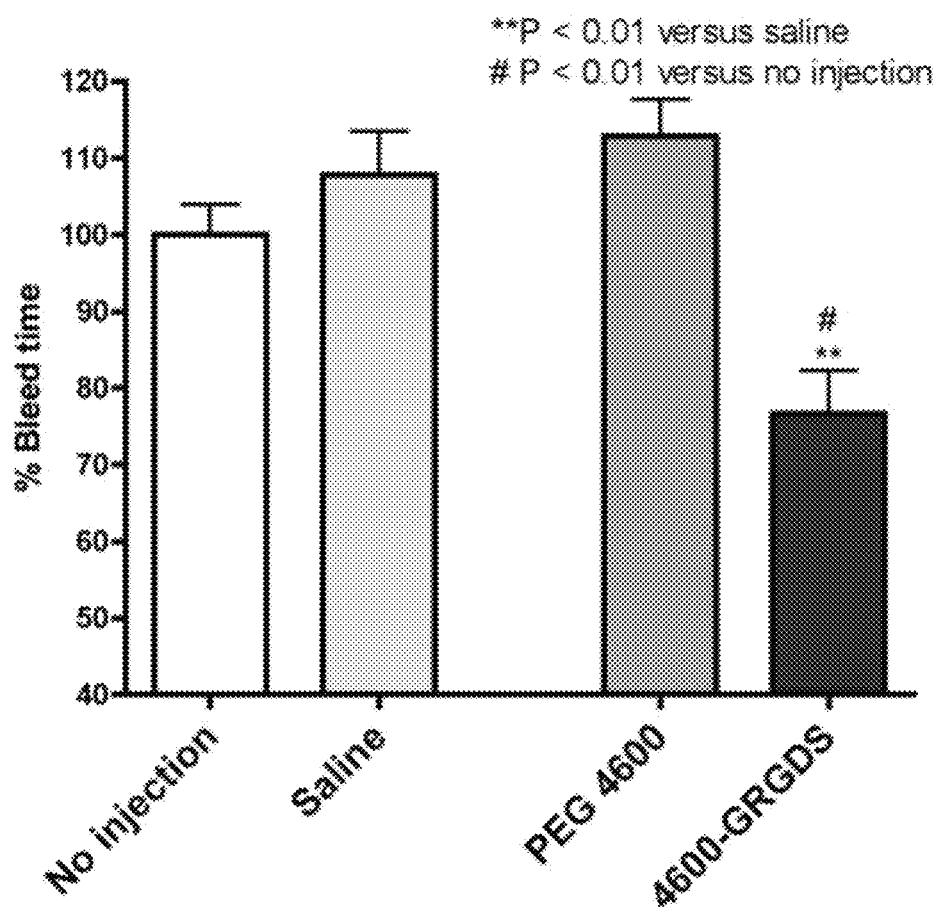

The effect these nanoparticles had on bleeding time was compared to saline control, recombinant Factor VIIa and nanoparticles which comprised PEG alone. All of the nanoparticles comprising a RGD peptide significantly reduced bleeding time. The nanoparticles were either administered immediately prior to injury (see FIG. 2A) or post-injury (see FIG. 2B). When administered post-injury, the nanoparticle comprising the 4600-GRGDS peptide significantly reduced % bleed time compared to nanoparticles only comprising PEG (PEG 4600). (See FIG. 2B)

TABLE 5

| | Survival Time (min) | | | Blood Loss (ml) | | |
|---|---|---|---|---|---|---|
| Dose (mg/kg) | Mean | S.D. | N | Mean | S.D. | N |
| Saline Control | 240 | 0 | 4 | 775 | 224.7 | 4 |
| NP1 Scrambled | | | | | | |
| 0.03 | 210 | | 1 | 1260 | | 1 |
| 0.10 | 26 | 28.3 | 3 | 920 | 408.4 | 3 |
| 0.20 | 7 | | 1 | 880 | | 1 |
| 2.00 | 8 | | 1 | 1040 | | 1 |
| GRGDS (SEQ ID NO: 2) | | | | | | |
| 0.03 | 30 | | 1 | 1240 | | 1 |
| 0.10 | 144 | 93.1 | 3 | 853 | 391.1 | 3 |
| 0.20 | 240 | | 1 | 1020 | | 1 |
| 2.00 | 9 | 0.0 | 2 | 890 | 14.1 | 2 |
| NP100 Scrambled | | | | | | |
| 0.10 | 73 | 77.6 | 5 | 1335 | 168.6 | 5 |
| 0.20 | 87 | | 1 | 820 | | 1 |
| GRGDS (SEQ ID NO: 2) | | | | | | |
| 0.10 | 172 | 81.4 | 6 | 1086 | 545.6 | 6 |
| 0.20 | 87 | 132.2 | 3 | 992 | 246.0 | 3 |

The initial hypothesis for this adverse response was that the particles may have been causing saturation of platelet receptors, as would be seen with administration of free RGD peptide, causing platelet inhibition. We therefore proceeded with our dosing study as planned, and found 0.1-0.2 mg/kg to be the "optimal" dose which did not elicit an adverse response. However, upon further analysis, the particles still appear to prolong bleeding times in the pigs, demonstrating increased amounts of bleeding post-treatment (5-60 min).

Several particle controls (2 mg/kg) that contained no targeting peptide were tested, suspecting that even the GRADSP (SEQ ID NO: 3) peptide may still be interacting with platelet receptors. However, it was observed that the nanoparticles induced a hemorrhagic response, regardless of the fact they contained no-peptide. Thus, the adverse effects are likely from a nonspecific interaction of the nanoparticles' material itself, leading to the development of a naive administration model to further investigate the phenomenon.

What is claimed:

1. A dry spray composition comprising a (i) nanoparticle comprising a co-block polymer core coupled to a water-soluble polymer and a peptide and (ii) a polycation, wherein the co-block polymer is PLGA, the water soluble polymer is PEG, the peptide comprises the sequence GRGDS, the polycation is polylysine; and the composition is stable at room temperature for at least 14 days.

2. The dry spray composition of claim 1, wherein the water soluble polymer of having sufficient length to allow binding of the peptide to glycoprotein IIb/IIIa (GPIIb/IIIa), the composition further comprising a poloxamer.

3. The dry spray composition of claim 1 wherein the poloxamer is a non ionic triblock copolymer comprising a structure -[hydrophilic polymer-hydrophobic polymer-hydrophilic polymer]n-.

4. The dry spray composition of claim 1 wherein the nanoparticle further comprises a therapeutic compound.

5. The dry spray composition of claim 4, wherein the therapeutic compound is covalently attached to the nanoparticle, non-covalently associated with the nanoparticle, associated with the nanoparticle through electrostatic interaction, or associated with the nanoparticle through hydrophobic interaction.

6. A method of treating a condition in an individual comprising the step of administering a composition of claim 1 to a patient in need thereof in an amount effective to treat the condition.

7. The method of claim 6, wherein the individual has a bleeding disorder.

8. The method of claim 7, wherein the composition is administered in an amount effective to reduce bleeding time by more than 15% compared to no administration or administration of saline.

9. The method of claim 7 wherein the bleeding disorder is a symptom of a clotting disorder, thrombocytopenia, a wound healing disorder, trauma, blast trauma, a spinal cord injury or hemorrhaging.

* * * * *

SEQUENCE LISTING

```
<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Gly Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Gly Arg Gly Asp Ser Pro
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Gly Arg Gly Asp Ser Pro Lys
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Gly Arg Gly Asp Asn
1               5

<210> SEQ ID NO 6
<211> LENGTH: 6
```

```
<212> TYPE: PRT
<213> ORGANISM: Artificial Sequence
<220> FEATURE:
<223> OTHER INFORMATION: Synthetic peptide

<400> SEQUENCE: 6

Gly Arg Gly Asp Asn Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Gly Gly Gly Gly Arg Gly Asp Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Gly Arg Gly Asp Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Gly Arg Gly Asp Thr Pro
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Tyr Arg Gly Asp Ser
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

His His Leu Gly Gly Ala Lys Gln Ala Gly Asp Val
1               5                   10
```